United States Patent
Hoffman (10) Patent No.: US 11,331,176 B2
(45) Date of Patent: May 17, 2022

(54) EXTRAORAL SUCTION DEVICE AND SYSTEM FOR MANAGING AEROSOL EMISSIONS DURING DENTAL PROCEDURES

(71) Applicant: Ronald Hoffman, Murray, KY (US)

(72) Inventor: Ronald Hoffman, Murray, KY (US)

( * ) Notice: Subject to any disclaimer, the term of this patent is extended or adjusted under 35 U.S.C. 154(b) by 18 days.

(21) Appl. No.: 17/064,027

(22) Filed: Oct. 6, 2020

(65) Prior Publication Data

US 2022/0104927 A1    Apr. 7, 2022

(51) Int. Cl.
*A61C 17/06* (2006.01)
*A61G 15/10* (2006.01)

(52) U.S. Cl.
CPC ............ *A61C 17/096* (2019.05); *A61G 15/10* (2013.01)

(58) Field of Classification Search
CPC ............................... A61C 17/096; A61G 15/10
USPC .......................................................... 433/33
See application file for complete search history.

(56) References Cited

U.S. PATENT DOCUMENTS

| | | | | |
|---|---|---|---|---|
| 1,388,312 A | * | 8/1921 | Seeger | A61C 17/08 433/96 |
| 3,537,447 A | * | 11/1970 | Gauthier | A61G 15/14 128/847 |
| 3,890,712 A | * | 6/1975 | Lopez | A61C 17/08 433/92 |
| 4,226,590 A | * | 10/1980 | Hofmann | A61C 17/12 433/28 |
| 5,078,603 A | * | 1/1992 | Cohen | A61M 1/84 433/91 |
| 5,449,206 A | * | 9/1995 | Lockwood | F16L 11/18 138/120 |
| 5,547,375 A | * | 8/1996 | Schneider | A61C 17/08 433/96 |
| 5,636,627 A | * | 6/1997 | Rochester | A61M 16/009 128/205.27 |
| 5,688,121 A | * | 11/1997 | Davis | A61C 17/08 433/96 |

(Continued)

FOREIGN PATENT DOCUMENTS

JP    3600224 A    2/2004

OTHER PUBLICATIONS

Eightteeth, "VacStation Extraoral Dental vacuum System," available at http://www.eighteeth.com/VacStation/ (retrieved Oct. 20, 2020).

(Continued)

*Primary Examiner* — Matthew M Nelson
(74) *Attorney, Agent, or Firm* — Stites & Harbison, PLLC; Gary N. Stewart (57) ABSTRACT

An extraoral suction device for managing aerosol emissions during dental procedures includes: a conduit; an adapter in fluid communication with the conduit; and a mount for mounting the extraoral suction device to a dental chair. The adapter is configured to be placed in fluid communication with a vacuum source to provide suction to the extraoral suction device. The conduit can be selectively manipulated to assume and maintain a position without support from an individual or designated support structure. A dental professional can thus manipulate the conduit to maintain a position in front of the oral cavity of a patient seated in the dental chair to direct aerosols emitted from the oral cavity of the patient into the extraoral suction device instead of the surrounding environment. The extraoral suction device can thus be combined with a dental chair and vacuum source to provide an improved dental chair system for dental procedures.

19 Claims, 7 Drawing Sheets

(56) References Cited

U.S. PATENT DOCUMENTS

| | | | | |
|---|---|---|---|---|
| 5,931,670 | A * | 8/1999 | Davis | A61C 1/088 |
| | | | | 433/91 |
| 6,464,499 | B1 * | 10/2002 | Lu | A61L 9/16 |
| | | | | 433/92 |
| 7,744,371 | B1 * | 6/2010 | Griffin | A61C 17/08 |
| | | | | 433/91 |
| 10,925,701 | B2 * | 2/2021 | Thomas | A61C 17/13 |
| 2013/0164706 | A1 * | 6/2013 | Odabashian | A61M 1/76 |
| | | | | 433/92 |
| 2020/0253701 | A1 * | 8/2020 | Tevrizian | A61L 29/005 |

OTHER PUBLICATIONS

PH Dental Inc., "Reduce the Risks! Safety Comes First with the Pax 2000X Exraoral Dental Suction System," available at https://phdentalinc.com/extraoral-dental-suction-system/ (retrieved Oct. 20, 2020).

Zyris, "How to perform Standard Installation for Isolate 3," Youtube, Dec. 29, 2018, available at https://www.youtube.com/watch?v=UzONJk7WvCA&feature=emb_logo (retrieved Oct. 20, 2020).

Loc-Line, "2019 Loc-Line The Original Modular Hose System," 2019, available at https://www.loc-line.com/catalog/ (retrieved Oct. 20, 2020).

AflexX, A~flexX HVE Standard Kit (Extra-Oral System), available at https://aflexxassistarm.com/product/aflexx-hve-assist-arm-kit/ (retrieved Oct. 20, 2020).

Zyris, "Isolite 3 Illuminated Dental Isolation System," Zyris Isolated Systems, available at https://store.zyris.com/collections/frontpage/products/isolite-3-illuminated-dental-isolation-system-1 (retreived Oct. 20, 2020).

* cited by examiner

EXTRAORAL SUCTION DEVICE AND SYSTEM FOR MANAGING AEROSOL EMISSIONS DURING DENTAL PROCEDURES

BACKGROUND OF THE INVENTION

The present invention relates to a device and system for use during dental procedures. More specifically, the present invention relates to an extraoral suction device and system for managing aerosol emissions.

Dental office examination rooms typically include a dental chair system that acts as the primary workstation where a patient's teeth can be examined and a variety of dental procedures can be performed. Common components of most modern dental chair systems include: a dental chair for seating a patient; a light; a cuspidor; various dental tools for insertion into the patient's oral cavity; an air compressor, which is used to actuate dental tools operably connected thereto; a pedal for controlling actuation of the dental tools operably connected to the air compressor; and a vacuum source, which is configured to draw a vacuum and provide suction to dental tools in fluid communication therewith. During most dental procedures, a patient is required to maintain their oral cavity in an open position for an extended period of time while a dental professional works on their teeth. As a result, aerosols are commonly emitted from the patient's oral cavity into the surrounding environment where they can subsequently be inhaled or ingested by the dental professional. Accordingly, in instances where the patient is sick, the emitted aerosols create a potential route for disease transmission from the patient to the dental professional.

Intraoral suction devices, such as conventional high-volume evacuators designed for insertion into the patient's oral cavity, are sometimes used to manage aerosol emissions. Often, such devices include a tip that is in fluid communication with a vacuum source providing suction and is inserted in the patient's oral cavity to collect fluids and particulates during the dental procedure. Generally, intraoral devices of known construction must either be manually held by a dental professional or deposited and left in the patient's oral cavity during the dental procedure. The former is problematic in instances where a servicing dental office is operating with a limited or reduced staff, and the latter can make for an unpleasant or even intolerable experience for some patients.

Recently, the use of extraoral suction systems designed to be positioned in proximity to patient's oral cavity to collect emitted aerosols has become increasingly popular. The dental chair systems utilized in most dental offices often occupy a large portion of the available working space within the examination rooms in which such systems are implemented. Extraoral suction systems of known construction are generally not configured to integrate with or utilize the components of existing dental chair systems. Rather, these systems typically exist as independent, self-contained systems, which, in use, are positioned on the floor adjacent to an existing dental chair system, thus further limiting the amount of available working space within the examination room.

Accordingly, there remains a need for an improved device and system for managing aerosol emissions during dental procedures.

SUMMARY OF THE INVENTION

The present invention is an extraoral suction device for managing aerosol emissions during dental procedures.

An extraoral suction device for managing aerosol emissions during dental procedures includes: a conduit; an adapter in fluid communication with the conduit; and a mount for mounting the extraoral suction device to a dental chair. The adapter is configured to be placed in fluid communication with a vacuum source, such that, when the vacuum source draws a vacuum, suction is provided to the extraoral suction device. The conduit can be selectively manipulated to assume and maintain a self-supported (i.e., without the support of an individual or designated support structure) position. A dental professional can thus manipulate the conduit to maintain a position in front of the oral cavity of a patient seated within the dental chair during a dental procedure to direct, via suction provided by the vacuum source, aerosols emitted from the oral cavity of the patient into the extraoral suction device, instead of the surrounding environment. In this way, the extraoral suction device thus manages aerosol emissions and mitigates the risk of disease transmission during dental procedures. As the extraoral suction device is configured for integration with structural features common in most modern dental chair systems (i.e., a dental chair and vacuum source), the extraoral suction device can be retrofitted to existing dental chair systems, thereby eliminating the need for independent, self-contained extraoral systems that occupy additional space within an examination room.

The conduit includes an inlet which provides an initial point of entry for aerosols into the extraoral suction device and an outlet for emitting aerosols into the adapter. The adapter also includes an inlet connected to the outlet of the conduit. In some embodiments, the conduit of the extraoral suction device includes a body portion, a nozzle, and an elbow that interconnects the body portion and the nozzle. In some embodiments, the nozzle is oversized relative to the other components of the conduit and defines an opening with a greater opening than that of either an interior channel defined by the body portion and an interior channel defined by the elbow. To enable manipulation of the conduit, the body portion preferably includes a plurality of articulations. In some embodiments, the body portion of the conduit is defined by a plurality of couplers, with each coupler including a ball portion and a socket portion, and each articulation of the body portion of the conduit is defined by a connection between the ball portion of one coupler and the socket portion of another coupler.

The adapter includes an outlet configured to be placed in fluid communication with the vacuum source to provide suction to the extraoral suction device. In some embodiments, the outlet of the adapter is defined by a valve that includes a handle for opening and closing the valve to regulate the suction provided to the extraoral suction device by the vacuum source. In some embodiments, the valve is configured to be connected to a vacuum hose in fluid communication with the vacuum source. To facilitate repositioning of the outlet of the adapter relative to the conduit, the adapter preferably includes at least one articulation.

The mount is preferably configured to support the full weight of the extraoral suction device when mounted to the dental chair. In this regard, in some embodiments, the mount includes a magnet of sufficient strength, such that the mount is able to support the full weight of the extraoral suction device, but is still able to be selectively mounted to or removed from suitable surfaces of the dental chair as desired to facilitate repositioning of the extraoral suction device about the dental chair. In some embodiments, the mount is connected to the adapter.

The extraoral suction device can be combined with a dental chair and vacuum source to provide an improved dental chair system for dental procedures.

DETAILED DESCRIPTION OF THE INVENTION

The present invention is an extraoral suction device for a dental chair system for managing aerosol emissions during dental procedures.

Figure 1:
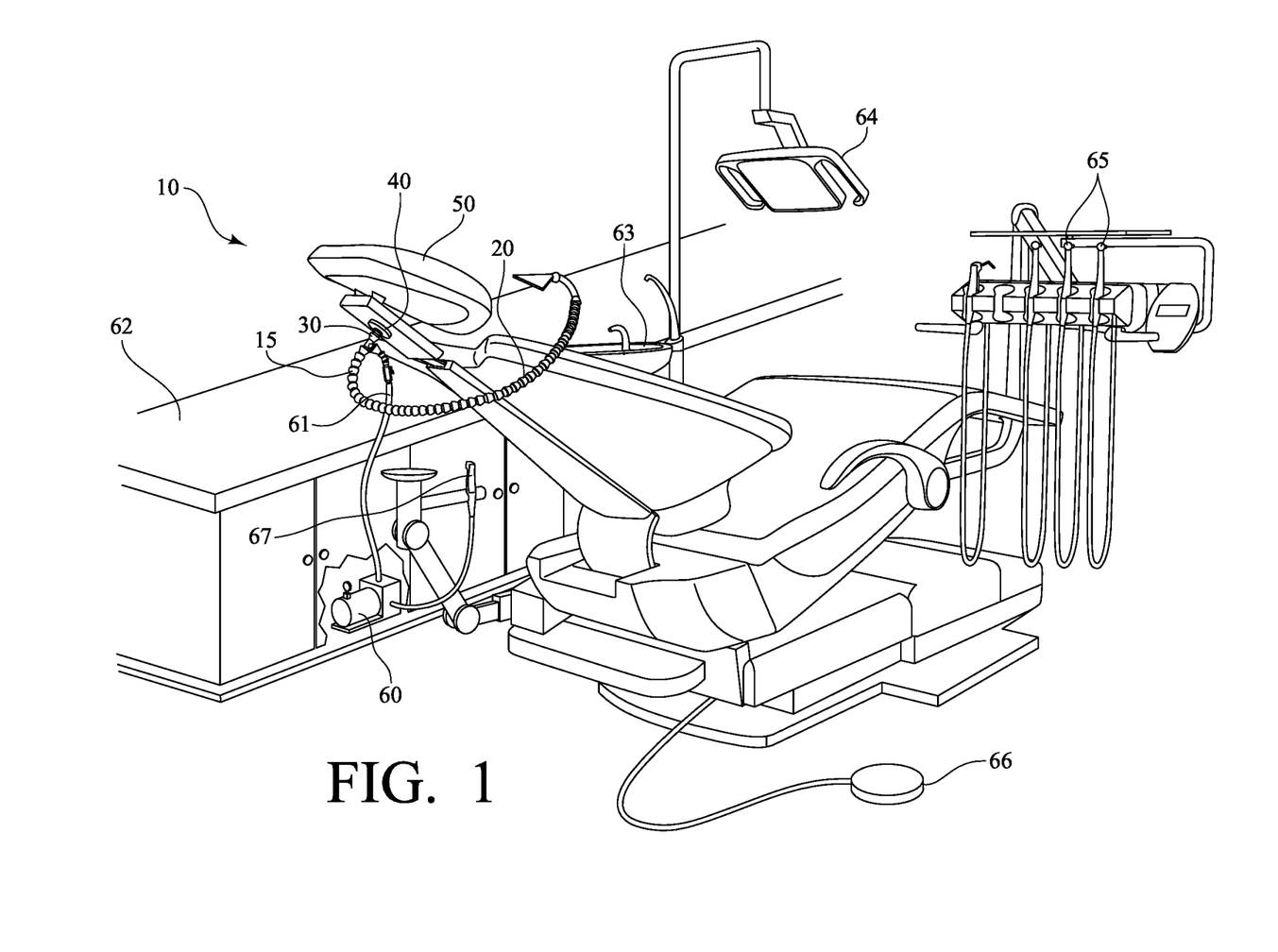
FIG. 1 is a perspective view of a dental chair system including an exemplary extraoral suction device made in accordance with the present invention.
Figure 2:
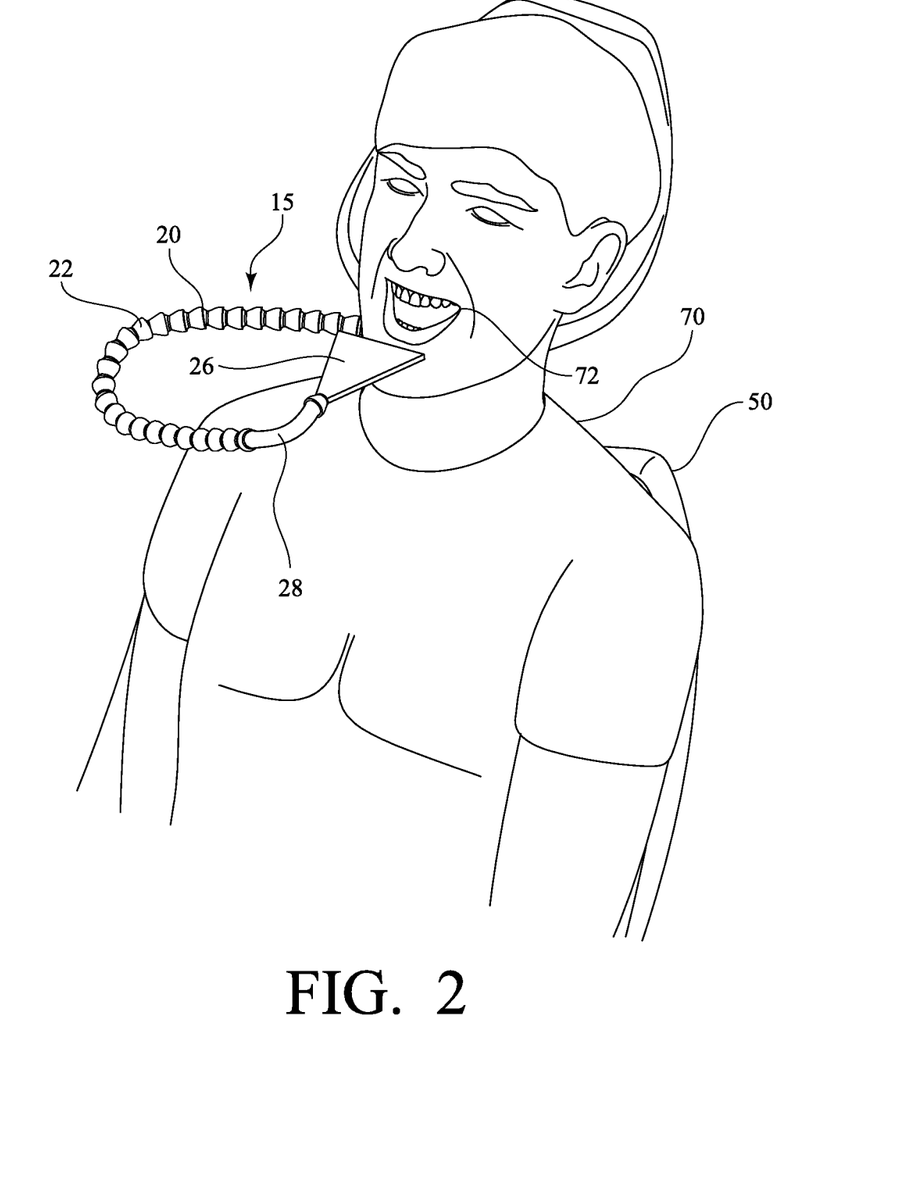
FIG. 2 is a perspective view of a portion of the dental chair system of FIG. 1, but with a patient seated in the dental chair of the dental chair system.

FIGS. 1 and 2 are perspective views of a dental chair system 10 for use during dental procedures, which includes an exemplary extraoral suction device 15 made in accordance with the present invention. As is common in most modern dental chair systems, the dental chair system 10 of the present disclosure includes a dental chair 50 for seating a patient 70 and a vacuum source 60 for drawing a vacuum. As shown in FIG. 1, in this exemplary embodiment, the dental chair system 10 further includes additional components commonly associated with a modern dental chair system (e.g., a cuspidor 63, a light 64, various dental tools 65 actuated by a compressor (not shown), a pedal 66 for controlling actuation of the compressor, and a saliva ejector 67 in fluid communication with the vacuum source 60). Such additional components are, however, not particularly relevant to the inventive subject matter disclosed herein, and are thus considered optional components of the dental chair system 10. In this embodiment, the vacuum source 60 is housed within a cabinet 62 positioned adjacent to the dental chair 50. Of course, the vacuum source 60 can be alternatively positioned without departing from the spirit or scope of the present invention. For example, in an alternative embodiment, the vacuum source 60 may be positioned below a floor surface on which the dental chair 50 rests.

Referring still to FIGS. 1 and 2, the extraoral suction device 15 is mounted to the dental chair 50 and is in fluid communication with the vacuum source 60, such that suction is provided to the extraoral suction device 15 (i.e., air is drawn into the extraoral suction device 15) when the vacuum source 60 draws a vacuum. In this exemplary embodiment, the extraoral suction device 15 is in fluid communication with the vacuum source 60 via a vacuum hose 61, such as that commonly used to interconnect the tip of a high-volume evacuator to a vacuum source. The extraoral suction device 15 includes a conduit 20 which can be selectively manipulated to assume and maintain a self-supported (i.e., without the support of an individual or designated support structure) position. A dental professional can thus manipulate the conduit 20 of the extraoral suction device 15 to maintain a position in front of an oral cavity 72 of the patient 70 during a dental procedure to direct, via suction provided by the vacuum source 60, aerosols emitted from the oral cavity 72 of the patient 70 into the extraoral suction device 15, instead of the surrounding environment. In this way, the extraoral suction device 15 thus manages aerosol emissions and mitigates the risk of disease transmission during dental procedures.

As the extraoral suction device 15 is configured for integration with structural features common in most existing dental chair systems (i.e., configured to be mounted to a dental chair and placed in fluid communication with a vacuum source), the extraoral suction device 15 of the present invention can thus be readily implemented in most modern dental chair systems. In other words, the extraoral suction device 15 can be retrofitted to the existing dental chair systems present within most dental offices, thereby eliminating the need for independent, self-contained extraoral systems that occupy additional space within an examination room.

Figure 3A:
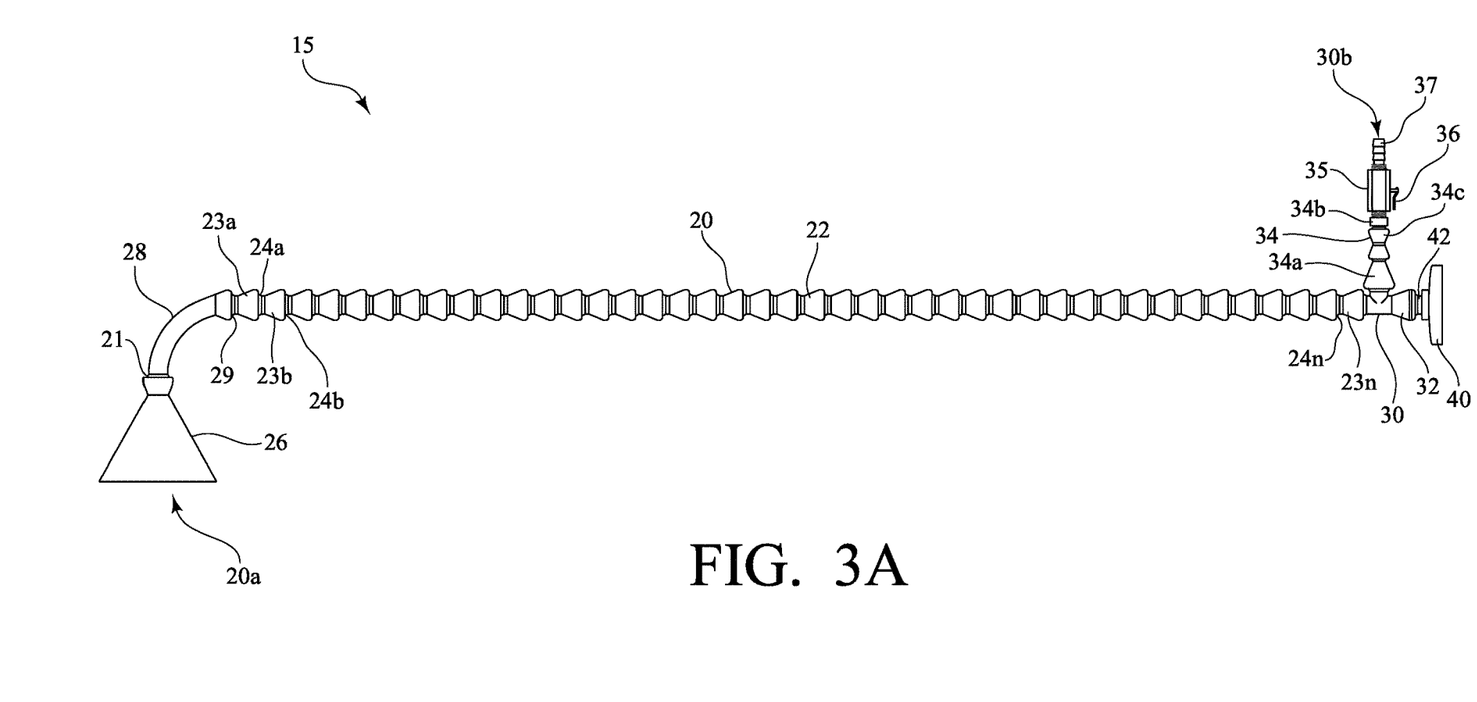
FIG. 3A is a side view of the exemplary extraoral suction device of the dental chair system of FIG. 1 in a first position and in isolation from the other components of the dental chair system 10 of FIG. 1.

FIG. 3A is a side view of the exemplary extraoral suction device 15 in a first position and in isolation from the other components of the dental chair system of FIG. 1.

Figure 3B:
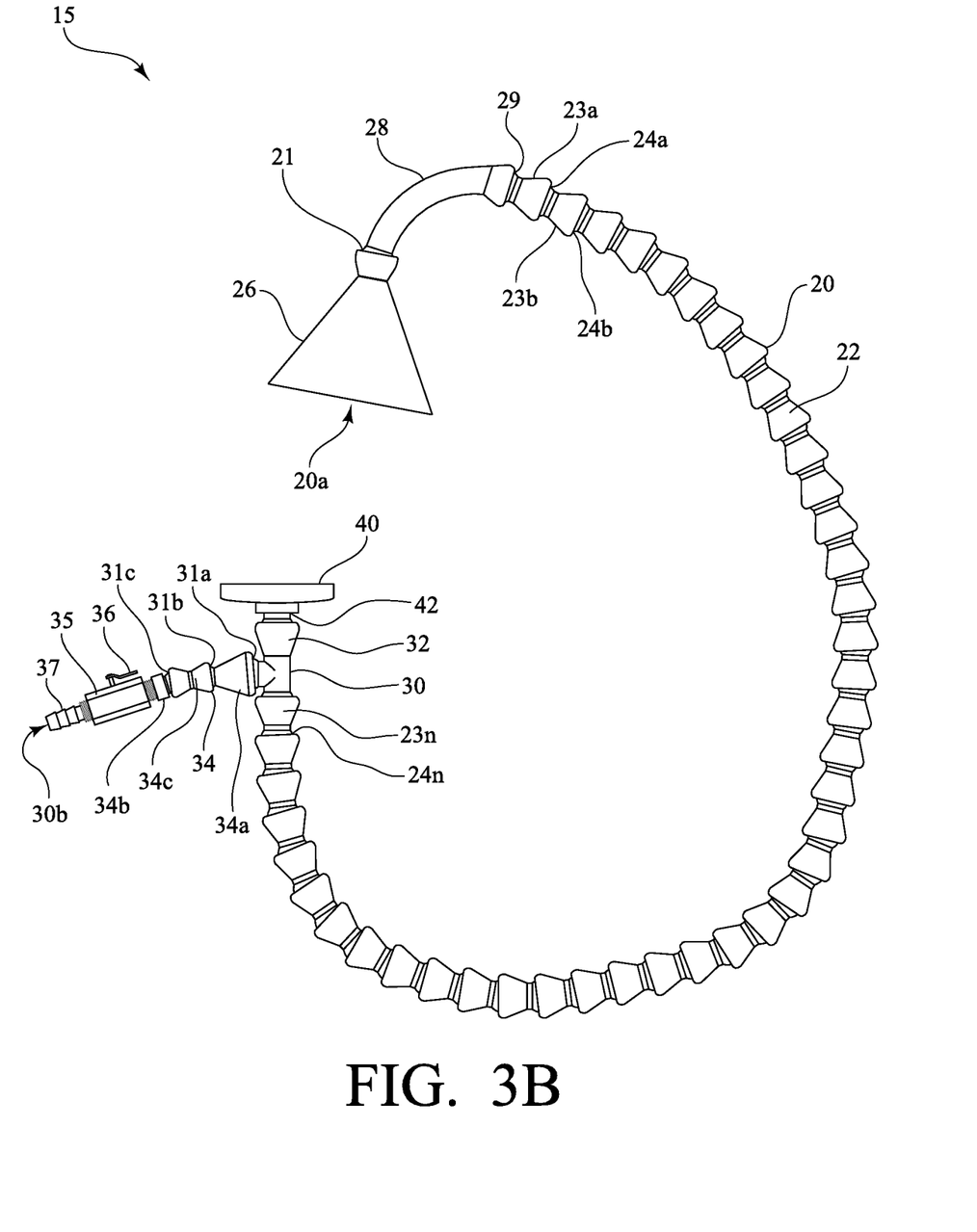
FIG. 3B is a side view of the exemplary extraoral suction device similar to FIG. 3A, but with the exemplary extraoral suction device 15 in a second position.

FIG. 3B is a side view of the exemplary extraoral suction device 15 similar to FIG. 3A, but with the exemplary extraoral suction device in a second position.

Figure 4:
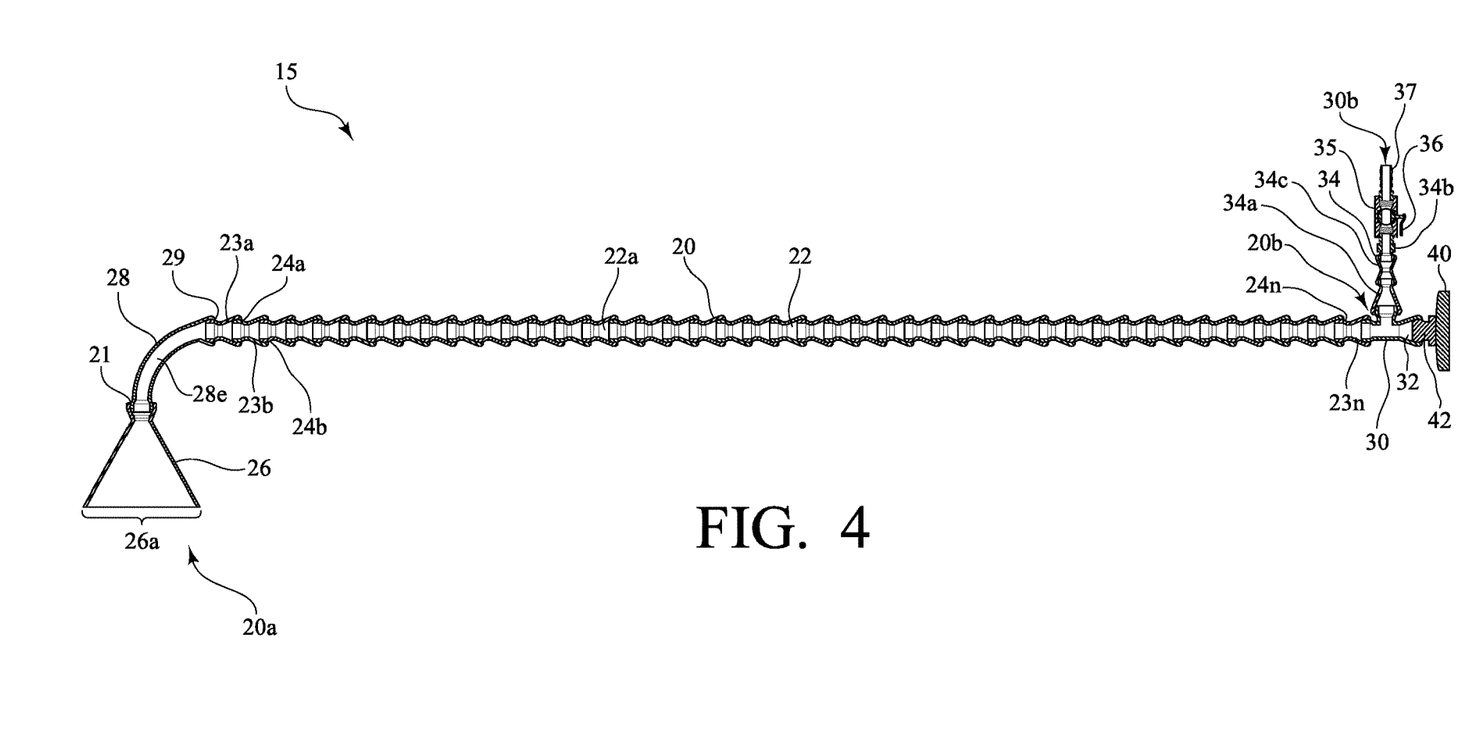
FIG. 4 is a sectional view of the exemplary extraoral suction device of FIG. 3A.

FIG. 4 is a sectional view of the exemplary extraoral suction device 15 of FIG. 3A.

Figure 5:
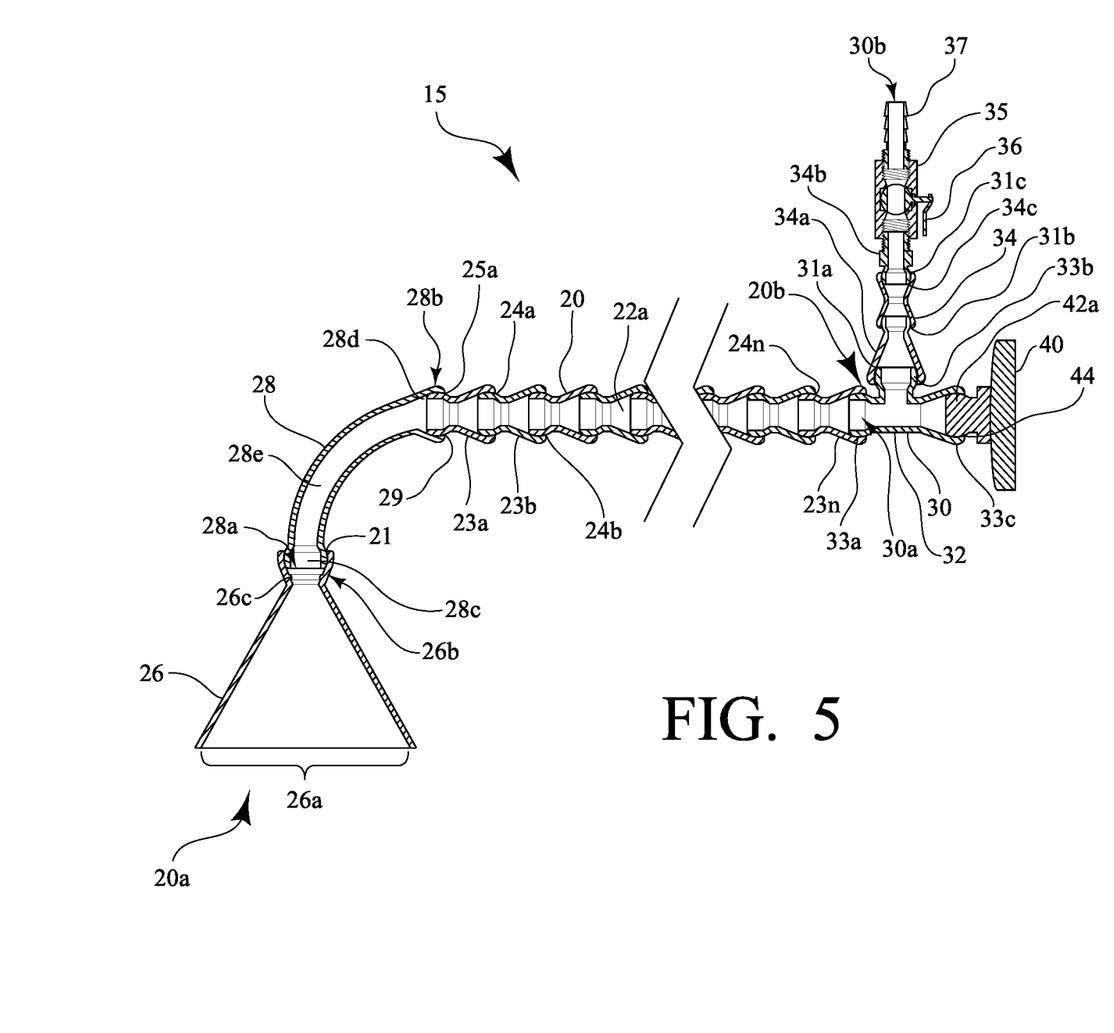
FIG. 5 is a partial magnified view of the exemplary extraoral suction device 15 of FIG. 4.

FIG. 5 is a partial magnified view of the exemplary extraoral suction device of FIG. 4.

Referring now to FIGS. 1, 2, 3A, 3B, 4, and 5, the extraoral suction device 15 includes the conduit 20, an adapter 30 that is in fluid communication with the conduit 20 and is configured to be placed in fluid communication with the vacuum source 60; and a mount 40 for mounting the extraoral suction device 15 to the dental chair 50. In this exemplary embodiment, the conduit 20 is defined by, and thus can be characterized as including, a body portion 22, a nozzle 26, and an elbow 28 interconnecting the body portion 22 to the nozzle 26. The nozzle 26 defines an inlet 20a of the conduit 20 that can be positioned in front of the oral cavity 72 of the patient 70 to draw in, via suction provided by the vacuum source 60, aerosols emitted from the oral cavity 72 of the patient 70 into the extraoral suction device 15. Aerosols entering into the inlet 20a of the conduit 20 travel through the respective components of the conduit 20 and are subsequently emitted out of the conduit 20 and into the adapter 30 via an outlet 20b defined by the body portion 22. In this regard the adapter 30 also includes an inlet 30a which is connected to the outlet 20b of the conduit 20, such that aerosols emitted from the conduit 20 are directed into the adapter 30. Aerosols entering the adapter 30 are subsequently emitted therefrom via an outlet 30b, which, as shown in FIG. 1, in this exemplary embodiment, is in fluid communication with the vacuum hose 61 interconnecting the extraoral suction device 15 to the vacuum source 60. It is contemplated, however, that, in some embodiments, the extraoral suction device 15 may be connected directly to the vacuum source 60.

As shown by viewing FIGS. 3A and 3B in sequence, the body portion 22 of the conduit 20 can be manipulated to alter the shape of the conduit 20 and reposition the inlet 20a of the conduit 20 relative to the oral cavity 72 of the patient 70 (FIG. 2). In this regard, the body portion 22 includes a plurality of articulations 24a, 24b, 24n (joints), only three of which are provided with reference numerals, that can be selectively manipulated to shape or reposition the body portion 22, and thus the conduit 20 as a whole. In this exemplary embodiment, the body portion 22 of the conduit 20 is defined by a plurality of couplers 23a, 23b, 23n, only three of which are provided with reference numerals, with each coupler 23a, 23b, 23n connected to and in fluid communication with at least one adjacent coupler 23a, 23b, 23n. In this exemplary embodiment, the body portion 22 of the conduit is defined by a total of forty-two couplers. Of course, the number of couplers 23a, 23b, 23n can be increased or decreased as desired to increase or decrease the overall length of the conduit 20 as needed.

Figure 6:
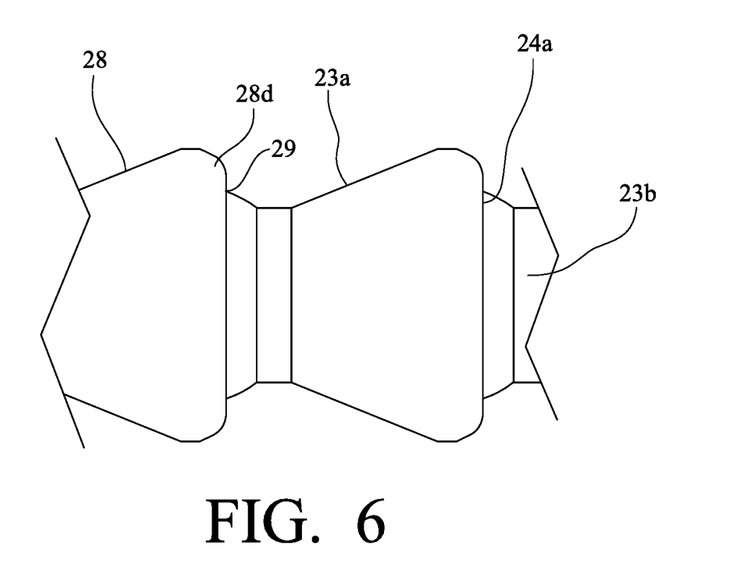
FIG. 6 is a partial view of the conduit of the exemplary extraoral suction device of FIG. 3A.

FIG. 6 is a partial view of the conduit of the exemplary extraoral suction device 15 of FIG. 3A.

Figure 7:
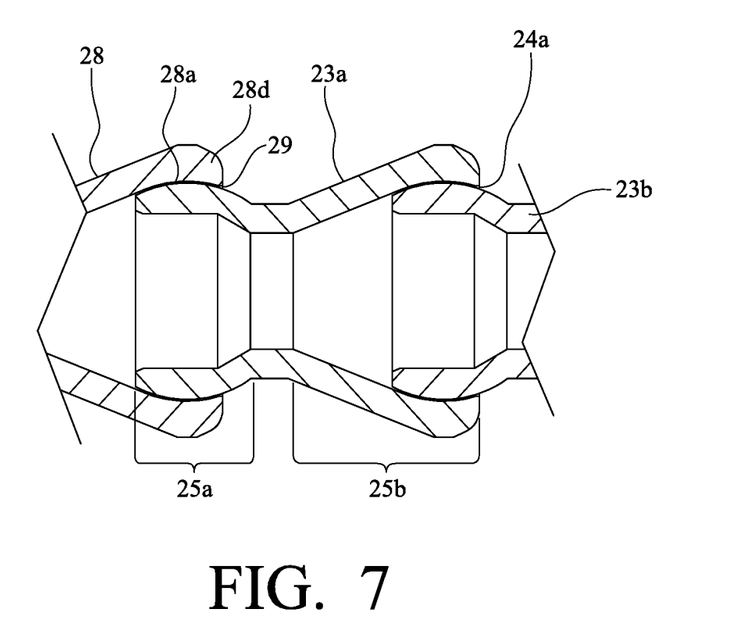
FIG. 7 is a sectional view of the conduit of FIG. 6.

FIG. 7 is a sectional view of the conduit of FIG. 6.

Referring now specifically to FIGS. 3A, 3B, and 4-7, one coupler 23a (or leading coupler) defines the outermost portion of one end of the body portion 22 and connects the body portion 22 to the elbow 28 while another coupler 23n (or trailing coupler) defines the outermost portion of another end of the body portion 22 and connects the body portion 22 to the inlet 30a of the adapter 30. As perhaps shown best in FIG. 7, in this exemplary embodiment, the leading coupler 23a is a ball-and-socket coupler, such as that manufactured and distributed by Lockwood Products Inc. of Lake Oswego, Oreg. In this regard, the leading coupler 23a is defined by, and thus can be characterized as including, a ball portion 25a and a socket portion 25b. In this exemplary embodiment, the respective couplers 23a, 23b, 23n defining the body portion 22 of the conduit 20 are identical. Accordingly, the other couplers 23b, 23n defining the body portion 22 of the conduit 20 likewise include a ball portion and a socket portion. In this exemplary embodiment, each articulation 24a, 24b, 24n of the body portion 22 is defined by a connection established by the insertion of the ball portion of one coupler into the socket portion of an adjacent coupler, as perhaps best shown by the articulation 24a formed by the insertion of the ball portion of coupler 23b into the socket portion 25b of coupler 23a in FIG. 7. The dimensions of the ball portion 25a and socket portion 25b of each respective coupler 23a, 23b, 23n defining the body portion 22 of the conduit 20 are such that, when the articulation 24a, 24b, 24n defined by the connection between two adjacent couplers 23a, 23b, 23n is manipulated, the couplers 23a, 23b, 23n corresponding to the articulation 24a, 24b, 24n retain the manipulated position. As a result, and referring now to FIGS. 1 and 2, when the body portion 22 is manipulated to place the conduit 20 in front of the oral cavity 72 of the patient 70, the conduit 20 is able to retain such position without support from a dental professional, the oral cavity 72 of the patient 70, or separate support structure. As a result, the extraoral suction device 15 can thus be utilized during dental procedures even in instances where a dental office is operating with a limited or reduced staff, or the patient is particularly sensitive to having objects disposed in their oral cavity for prolonged periods of time.

Referring now to FIGS. 1, 2, 3A, 3B, and 4-7, as noted above, in this exemplary embodiment the nozzle 26 is connected to the body portion 22 of the conduit 20 via the elbow 28, which, in this case, is a 90° elbow with a first end connected to the leading coupler 23a and a second end connected to the nozzle 26. Of course, other types of elbows or conduits may be utilized to accommodate different applications and/or environments and interconnect the nozzle 26 to the body portion 22 of the conduit 20 without departing from the spirit or scope of the present disclosure. Indeed, it is contemplated that, in some alternative embodiments, no elbow is utilized at all and the nozzle 26 is directly connected to the body portion 22 of the conduit 20.

Referring now to FIGS. 3A, 3B, 4, and 5, in this exemplary embodiment the elbow 28 includes an inlet 28a defined by a ball portion 28c of the elbow 28 into which aerosols are received into the elbow 28 from the nozzle 26 and an outlet 28b defined by a socket portion 28d of the elbow 28 through which aerosols are emitted from the elbow 28 into the body portion 22 of the conduit 20. The ball portion 28c of the elbow 28 is connected with a socket portion 26c defining an outlet 26b of the nozzle 26 to form an articulation 21 which enables the positioning of the nozzle 26 to be adjusted relative to the elbow 28. The socket portion 28d of the elbow 28 is coupled with the ball portion 25a of the leading coupler 23a of the body portion 22 to form an articulation 29 which enables the positioning of the elbow 28 to be adjusted relative to the body portion 22 of the conduit 20.

Referring now again to FIGS. 1, 2, 3A, 3B, 4 and 5, to facilitate increased capture of aerosols into the inlet 20a of the conduit, in this exemplary embodiment, the nozzle 26 is oversized relative to the other components of the conduit 20. In this regard, the nozzle 26 defines an opening 26a having a greater diameter than that of either an interior channel 22a defined by the body portion 22 of the conduit 20 or an interior channel 28e defined by the elbow 28, as shown best in FIGS. 4 and 5.

Referring now again to FIGS. 3A, 3B, 4, and 5, in this exemplary embodiment, the adapter 30 includes a tee fitting 32 and a valve 35. In this embodiment, the tee fitting 32 includes a first ball portion 33a which defines a first opening that serves as the inlet 30a of the adapter 30. The first ball portion 33a is connected to the socket portion of the trailing coupler 23n of the body portion 22 of the conduit 20. As shown in FIGS. 4 and 5, the first ball portion 33a of the tee fitting 32 is of similar construction as the ball portions of the plurality of couplers 23a, 23b, 23n. As such, the connection between the first ball portion 33a of the tee fitting 32 and the socket portion of the trailing coupler 23n define an articulation, which enables the conduit 20 to be repositioned relative to the adapter 30. To facilitate emission of aerosols from the tee fitting 32 into the valve 35, the tee fitting 32 also includes a second ball portion 33b which defines a second opening which, in this case, is perpendicular relative to the first opening defining the inlet 30a of the adapter 30.

Referring still to FIGS. 3A, 3B, 4, and 5, in this exemplary embodiment, the adapter 30 further includes an arm 34 that interconnects the tee fitting 32 to the valve 35, such that the tee fitting 32 and the valve 35 are in fluid communication with each other. In this embodiment, the arm 34 includes a first end 34a defining a socket portion in which the second ball portion 33b of the tee fitting 32 is connected and a second end 34b with threading compatible with threading of the valve 35. The connection between the socket portion defined by the first end 34a of the arm 34 and the second ball portion 33b of the tee fitting 32 form an articulation 31a which can be selectively manipulated to reposition the arm 34 and valve 35 relative to the tee fitting 32. In this exemplary embodiment, the arm 34 further includes an intermediary connector 34c which interconnects the first end 34a of the arm 34 to the second end 34b of the arm 34. The connection formed between the first end 34a and the intermediate connector 34c of the arm define a second articulation 31b. The connection formed between the second end 34b and the intermediate connector 34c of the arm 34 define a third articulation 31c. The second articulation 31b and the third articulation 31c of the arm 34 can also be selectively manipulated to reposition the arm 34 and valve 35 relative to the tee fitting 32 of the adapter 30.

Referring still to FIGS. 3A, 3B, 4, and 5, in this exemplary embodiment, the valve 35 includes a handle 36 and a tip 37. The handle 36 can be manipulated to selectively open or close the interior channel of the valve 35 to regulate the suction provided to the extraoral suction device 15 by the vacuum source 60. In this exemplary embodiment, the valve 35 is a ball valve, though other types of valves can alternatively be used without departing from the spirit and scope of the present invention. The tip 37 of the valve 35 defines the outlet 30b of the adapter 30 and is configured to be connected to the vacuum hose 61 to place the extraoral suction device 15 in fluid communication with the vacuum source 60.

As shown best in FIG. 1, to ensure the extraoral suction device 15 remains mounted to the dental chair 50 during dental procedures, without assistance from an individual or external support structure, the mount 40 is configured to support the full weight of the extraoral suction device 15 as well as the vacuum hose 61. In this exemplary embodiment, the mount 40 is a permanent magnet of sufficient magnetic strength, such that the mount 40 is able to support the full weight of the extraoral suction device 15 and the vacuum hose 61, but can be selectively mounted to or removed from suitable (e.g., metal) surfaces of the dental chair 50 as desired to reposition the extraoral suction device 15 about the dental chair 50. In this exemplary embodiment, and referring now to FIGS. 3A, 3B, 4, and 5, the mount 40 includes a bracket 42 which connects the mount 40 to the adapter 30. Specifically, the bracket 42 of the mount 40 defines, and thus can be characterized as including, a ball portion 42a which is connected to a socket portion 33c of the tee fitting 32, as shown in FIG. 5. The connection between the ball portion 42a of the bracket 42 and the socket portion 33c of the tee fitting 32 define an articulation 44, which enables the mount 40 to be repositioned relative to the adapter 30. Of course, the mount 40 may be alternatively connected to the adapter 30 without departing from the spirit or scope of the present invention.

One of ordinary skill in the art will recognize that additional embodiments are also possible without departing from the teachings of the present invention. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. An extraoral suction device for a dental chair system including a dental chair and a vacuum source, the extraoral suction device comprising:
   a conduit including an inlet for receiving aerosols emitted from an oral cavity of a patient and an outlet for emitting the aerosols from the conduit;
   an adapter including an inlet in fluid communication with the outlet of the conduit and an outlet configured to be placed in fluid communication with the vacuum source; and
   a mount for mounting the extraoral suction device to the dental chair;
   wherein the conduit is configured to maintain a self-supported position when the inlet of the conduit is placed in front of the oral cavity of the patient;
   wherein the extraoral suction device includes at least one of a first articulation defined by a connection between the conduit and the adapter, a second articulation defined by a connection between the mount and the adapter, and a third articulation defined by a connection between a first portion of the adapter and a second portion of the adapter;
   wherein, in use, the first articulation can be manipulated to reposition the conduit relative to the adapter, the second articulation can be manipulated to reposition the mount relative to the adapter, and the third articulation can be manipulated to reposition the first portion of the adapter relative to the second portion of the adapter.

2. The extraoral suction device as recited in claim 1, wherein the conduit includes a body portion including a plurality of articulations.

3. The extraoral suction device as recited in claim 2, wherein the body portion of the conduit is defined by a plurality of couplers, each coupler including a ball portion and a socket portion, and wherein each articulation of the body portion is defined by a connection between the ball portion of one coupler and the socket portion of another coupler.

4. The extraoral suction device as recited in claim 2, wherein the inlet of the conduit is defined by a nozzle, the nozzle being in fluid communication with the body portion of the conduit and defining an opening with a diameter greater than that of an interior channel defined by the body portion of the conduit.

5. The extraoral suction device as recited in claim 1, wherein the outlet of the adapter is defined by a valve including a handle for opening and closing the valve, the valve being configured to be connected to a vacuum hose in fluid communication with the vacuum source.

6. The extraoral suction device as recited in claim 1, wherein the conduit includes a body portion defining the outlet of the conduit, a nozzle defining the inlet of the conduit, and an elbow interconnecting the body portion to the nozzle, and wherein a connection between the elbow and the body portion define a fourth articulation allowing the elbow to be repositioned relative to the body portion, and a connection between the elbow and the nozzle define a fifth articulation allowing the nozzle to be repositioned relative to the elbow.

7. The extraoral suction device as recited in claim 1, wherein the mount includes a magnet, the magnet being of sufficient strength to support the full weight of the extraoral suction device when the magnet is mounted to the dental chair.

8. The extraoral suction device as recited in claim 1, wherein the mount is connected to the adapter.

9. The extraoral suction device as recited in claim 1, wherein the extraoral suction device includes at least two of the first articulation, the second articulation, and the third articulation.

10. The extraoral suction device as recited in claim 1, wherein the extraoral suction device includes the first articulation, the second articulation, and the third articulation.

11. An extraoral suction device for a dental chair system including a dental chair and a vacuum source, the extraoral suction device comprising:
   a conduit, including
      a nozzle defining an inlet for receiving aerosols emitted from an oral cavity of a patient, and a body portion including a plurality of articulations, the body portion being in fluid communication with the nozzle and defining an outlet for emitting the aerosols from the conduit;
an adapter including an inlet in fluid communication with the outlet of the conduit and an outlet configured to be placed in fluid communication with the vacuum source; and a mount for mounting the extraoral suction device to the dental chair connected to the adapter and being configured to support the full weight of the extraoral device when mounted to the dental chair;

wherein the conduit is configured to maintain a self-supported position when the nozzle is placed in front of the oral cavity of the patient;

wherein the extraoral suction device includes at least one of a first articulation defined by a connection between the conduit and the adapter, a second articulation defined by a connection between the mount and the adapter, and a third articulation defined by a connection between a first portion of the adapter and a second portion of the adapter;

wherein, in use, the first articulation can be manipulated to reposition the conduit relative to the adapter, the second articulation can be manipulated to reposition the mount relative to the adapter, and the third articulation can be manipulated to reposition the first portion of the adapter relative to the second portion of the adapter.

12. The extraoral suction device as recited in claim 11, wherein the outlet of the adapter is defined by a valve having a handle for opening and closing the valve.

13. The extraoral suction device as recited in claim 11, wherein the body portion of the conduit is defined by a plurality of couplers, each coupler including a ball portion and a socket portion, and wherein each articulation of the body portion is defined by a connection between the ball portion of one coupler and the socket portion of another coupler.

14. A dental chair system, comprising:

a dental chair;

a vacuum source; and an extraoral suction device, including a conduit including an inlet for receiving aerosols emitted from an oral cavity of a patient and an outlet for emitting the aerosols from the conduit, an adapter including an inlet in fluid communication with the outlet of the conduit and an outlet in fluid communication with the vacuum source, and a mount for mounting the extraoral suction device to the dental chair, wherein the conduit is configured to maintain a self-supported position when the inlet of the conduit is placed in front of the oral cavity of the patient;

wherein the extraoral suction device includes at least one of a first articulation defined by a connection between the conduit and the adapter, a second articulation defined by a connection between the mount and the adapter, and a third articulation defined by a connection between a first portion of the adapter and a second portion of the adapter;

wherein, in use, the first articulation can be manipulated to reposition the conduit relative to the adapter, the second articulation can be manipulated to reposition the mount relative to the adapter, and the third articulation can be manipulated to reposition the first portion of the adapter relative to the second portion of the adapter.

15. The dental chair system as recited in claim 14, and further comprising:

a vacuum hose interconnecting the vacuum source and the extraoral suction device.

16. The dental chair system as recited in claim 14, wherein the conduit of the extraoral suction device includes a body portion including a plurality of articulations.

17. The dental chair system as recited in claim 16, wherein the body portion of the conduit is defined by a plurality of couplers, each coupler including a ball portion and a socket portion, and wherein each articulation of the body portion is defined by a connection between the ball portion of one coupler and the socket portion of another coupler.

18. The dental chair system as recited in claim 16, wherein the inlet of the conduit is defined by a nozzle, the nozzle being in fluid communication with the body portion of the conduit and defining an opening with a diameter greater than that of an interior channel defined by the body portion of the conduit.

19. The dental chair system as recited in claim 14, wherein the mount is configured to support the full weight of the extraoral suction device when mounted to the dental chair.

* * * * *